United States Patent
Wood et al.

(10) Patent No.: US 6,440,984 B1
(45) Date of Patent: Aug. 27, 2002

(54) USE OF ARYL-SUBSTITUTED PYRIMIDINES AS INSECTICIDAL AND ACARICIDAL AGENTS

(75) Inventors: William Wakefield Wood, Pennington; Linda Fleming, Ewing; Salvatore John Cuccia, Lawrenceville, all of NJ (US)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/725,376

(22) Filed: Nov. 29, 2000

Related U.S. Application Data

(62) Division of application No. 09/036,490, filed on Mar. 6, 1998, now Pat. No. 6,306,866.

(51) Int. Cl.[7] ............... A61K 31/505; A01N 43/54; C07D 239/02

(52) U.S. Cl. ............ 514/269; 514/272; 514/274; 544/309; 544/311; 544/312; 544/314; 544/319; 544/321

(58) Field of Search .............. 514/269, 272, 514/274; 544/309, 311, 312, 314, 319, 321

(56) References Cited

U.S. PATENT DOCUMENTS

| 4,248,618 A | 2/1981 | Serban et al. ........ 544/315 |
| 4,427,437 A | 1/1984 | Serban et al. ........ 544/315 |
| 4,725,600 A | 2/1988 | Takaya et al. ........ 514/296 |
| 4,826,531 A | 5/1989 | Anthony et al. ...... 544/328 |

FOREIGN PATENT DOCUMENTS

| EP | 0 506 270 A1 | 9/1992 |
| EP | 0 723 960 A1 | 7/1996 |
| JP | 49021148 | 5/1974 |
| JP | 4095077 | 3/1992 |

OTHER PUBLICATIONS

Masuda et al, "Chemical Abstracts", vol. 117: abstract 171467 (1992).
Murata; Chemical Abstract, vol. 105: Abstract 78951 (1986).
Peereboom et al, Ring Transformations in ractions of heterocyclic halogeno compounds with nucleophiles, Laboratory of Organic Chemistry, Agricultural University, The Netherlands, pp. 284–287 (1974).
Tani et al, Chemical Abstracs, vol. 82 Entry 140173 (1974).
Wierenga et al., "Synthesis of 2–Amino–6–Phenyl–4(3H)–Pyrimidine–1–Oxide", Heterocycles, vol. 16, No. 4, 1981, pp. 563–571.
Kreutzberger et al., "Insecticidal Agents. I. Cyclization reactions with 4–nitrophenylguanidine", Chem.–Ztg. (1981), 105(7–8), 229–32.
Kreutzberger et. al., Chem. Abs., 1981, vol. 95, Abs. No. 169117.*

* cited by examiner

Primary Examiner—Mukund J. Shah
Assistant Examiner—Tamthom N. Truong
(74) Attorney, Agent, or Firm—Keil & Weinkauf

(57) ABSTRACT

There are provided compositions and methods comprising compounds of formula I:

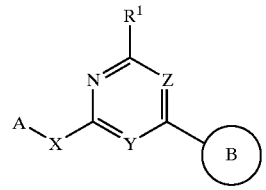

wherein $R^1$, A, B, X, Y and Z have the meaning given in claim 1, for the control of insect and acarid pests.

8 Claims, No Drawings

USE OF ARYL-SUBSTITUTED PYRIMIDINES AS INSECTICIDAL AND ACARICIDAL AGENTS

CROSS-REFERENCE TO RELATED APPLICATIONS

This is a divisional application of U.S. Ser. No. 09/036,490 filed Mar. 6, 1998, now U.S. Pat. No. 6,306,866.

BACKGROUND OF THE INVENTION

Insect and acarid pests destroy growing and harvested crops. In the United States, agronomic crops must compete with thousands of those pests. In particular, tobacco budworms and southern armyworms are especially devastating to crops.

Tobacco budworms cause tremendous economic losses in agronomic crops. In particular, budworms devastate cotton crops by feeding on green bolls. Control of budworms is complicated by their resistance to many common insecticides, including organophosphates, carbamates and pyrethroids.

In spite of the commercial insecticides and acaricides available today, damage to crops, both growing and harvested, caused by insect and acarid pests still occurs. Accordingly, there is ongoing research to create new and more effective insecticidal and acaricidal agents.

Certain pyrimidine compounds are known to possess insecticidal and nematocidal activity (see, e.g., EP 0 506 270). However, none of those compounds are within the scope of the present invention.

It is, therefore, an object of the present invention to provide compounds which are highly effective for the control of insect and acarid pests.

It is also an object of the present invention to provide a method for the control of insect and acarid pests.

It is a further object of this invention to provide a method for the protection of growing and harvested crops from damage caused by insect and acarid attack and infestation.

Those and other objects of the present invention will become more apparent from the detailed description thereof set forth below.

SUMMARY OF THE INVENTION

This application is also related to application Ser. No. 09/273,942, filed Mar. 22, 1999, now U.S. Pat. No. 6,153,619.

The present invention describes aryl pyrimidines which are useful as insecticidal and acaricidal agents. Those compounds are also useful for protecting plants from damage caused by insect and acarid attack and infestation.

The aryl pyrimidines used according to the present invention have the structural formula I

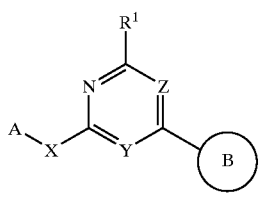

(I)

wherein
A and B each independently represent an optionally substituted aryl group;

$R^1$ represents a hydrogen or halogen atom or an optionally substituted alkyl, alkenyl, alkinyl, alkoxy, alkoxyalkyl, alkoxyalkoxy group; or an alkylthio group, alkylsulphinyl or alkylsulphonyl group, an amino, alkylamino or dialkylamino group or a cyano, nitro, haloalkyl, haloalkoxy, haloalkylthio or SF5 group, one of Y and Z represents N and the other represents $CR^2$, in which $R^2$ has the meaning given for $R^1$;

X represents O or NR, in which R represents a hydrogen atom or an alkyl group.

This invention also describes compositions containing those compounds and methods for using those compounds and compositions. Advantageously, it has been found that the pyrimidine compounds of the present invention, and compositions containing them, are useful for the control of insect and acarid pests. The compounds of this invention are also useful for the protection of plants from damage caused by insect and acarid attack and infestation. The pyrimidine compounds are especially useful for the control of tobacco budworms and southern armyworms.

DETAILED DESCRIPTION OF THE INVENTION

The present invention provides a method for the control of insect or acarid pests which comprises contacting said pests or their food supply, habitat or breeding grounds with a pesticidally effective amount of an aryl pyrimidine of formula I.

The present invention also provides a method for the protection of growing plants from attack or infestation by insect or acarid pests which comprises applying to the foliage of the plants, or to the soil or water in which they are growing, a pesticidally effective amount of an aryl pyrimidine compound of formula I.

The aryl pyrimidines of the present invention have the structural formula I

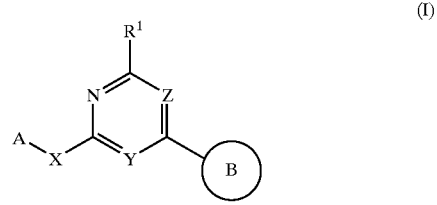

(I)

wherein A, B, X, Y, Z and $R^1$ are as described hereinabove for formula I.

Exemplary of halogen hereinabove are fluorine, chlorine, bromine and iodine.

Preferred formula I aryl pyrimidines of the present invention are those wherein
A and B are each independently phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups;

$R^1$ and $R^2$ are each independently hydrogen, $C_1$–$C_4$alkyl, $C_1$–$C_4$alkoxy, $C_1$–$C_4$alkylthio, cyano, nitro, amino, $C_1$–$C_4$haloalkyl, $C_1$–$C_4$haloalkoxy or fluorine; and A is phenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, B is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups.

More preferred insecticidal and acaricidal agents of the present invention are those wherein A is phenyl optionally substituted with any combination of from one to three halogen, $C_1$–$C_4$alkyl, $C_1$–$C_4$haloalkyl, $C_1$–$C_4$alkoxy, $C_1$–$C_4$alkylthio or $C_1$–$C_4$haloalkoxy groups;

$R^1$ and $R^2$ each independently are hydrogen, methyl ethyl, fluoro, chloro, cyano, nitro, amino, thiomethyl or trifluoromethyl;

preferably at least one of $R^1$ and $R^2$ is hydrogen; and

A and B are each independently phenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups.

The terms "$C_1$–$C_4$haloalkyl" and "$C_1$–$C_4$haloalkoxy" are defined as a $C_1$–$C_4$alkyl group and a $C_1$–$C_4$alkoxy group substituted with one or more halogen atoms, respectively.

Formula I compounds of this invention which are particularly effective insecticidal agents include the novel compounds of formulae IA and IB:

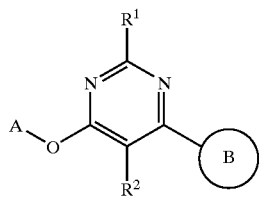
(IA)

$R^1$ and $R^2$ each independently represents a hydrogen or halogen atom or an alkyl, alkenyl, alkinyl, alkoxy, alkoxyalkyl, alkoxyalkoxy group, alkylthio, alkylsulphinyl or alkylsulphonyl group, an amino, alkylamino or dialkylamino group or a cyano, nitro, haloalkyl, haloalkoxy, haloalkylthio or $SF_5$ group, A represents a phenyl group being substituted by one or more of the same or different substituents selected from halogen atoms, alkyl, alkoxy, cyano, nitro, haloalkyl, haloalkoxy, alkylthio, haloalkylthio, alkylsulphinyl, alkylsulphonyl and $SF_5$ groups; and B represents a phenyl group being substituted by one or more of the same or different substituents selected from halogen atoms, alkyl, alkoxy, cyano, nitro, haloalkyl, haloalkoxy, alkylthio, haloalkylthio, alkylsulphinyl, alkylsulphonyl and $SF_5$ groups;

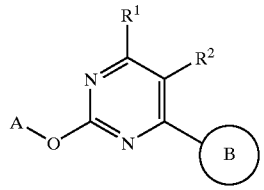
(IB)

wherein $R^1$ and $R^2$ have the meaning given in claim 1; A represents a phenyl group being substituted by one or more of the same or different substituents selected from halogen atoms, alkyl, alkoxy, cyano, nitro, haloalkyl, haloalkoxy, alkylthio, haloalkylthio, alkylsulphinyl, alkylsulphonyl and $SF_5$ groups; and B represents a phenyl group being substituted by one or more of the same or different substituents selected from halogen atoms, alkyl, alkoxy, cyano, nitro, haloalkyl, haloalkoxy, alkylthio, haloalkylthio, alkylsulphinyl, alkylsulphonyl and $SF_5$ groups.

Particularly preferred are the compounds of formulae IA1 and IA2

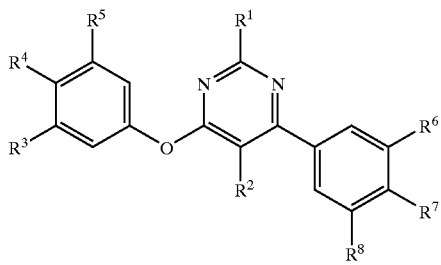
(IA1)

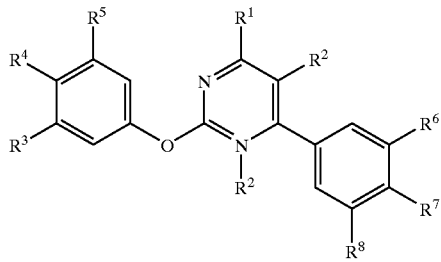
(IB1)

in which $R^1$ and $R^2$ have the meaning given for formulae IA and IB; and $R^3$ through $R^8$ each independently represent a hydrogen or halogen atom, in particular F or Cl, or a $C_{1-4}$ alkyl, in particular methyl or ethyl, a $C_{1-4}$ alkoxy, in particular methoxy or ethoxy, a $C_{1-4}$ haloalkyl, in particular trifluoromethyl, a $C_{1-4}$ haloalkoxy, in particular difluoro- or trifluoromethoxy, a cyano or nitro group.

Preferably at least one of the groups $R^3$, $R^4$ and $R^5$ is different from a hydrogen atom and at least one of the groups $R^6$, $R^7$ and $R^8$ is different from a hydrogen atom.

Advantageously, it has been found that the formula I compounds of the present invention are especially useful for the control of tobacco budworms and southern armyworms.

Aryl pyrimidines of the present invention wherein Y is $CR^1$ and Z is N (formula IA) may be prepared by reacting a compound of formula IIA

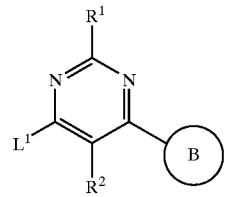
(IIA)

in which B, $R^1$ and $R^2$ have the meaning given and $L^1$ is a leaving group, with a compound of general formula IIIA,

A—$OM^1$            IIIA wherein

A is defined as for formula IA; and $M^1$ represents a hydrogen or a metal atom.

Furthermore, the invention relates to a process for the preparation of a compound of general formula IB, which comprises reacting a respective compound of the general formula IIB,

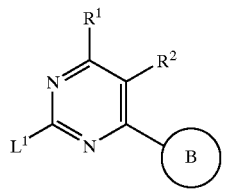

(IIB)

in which B, R$^1$ and R$^2$ have the meaning given and L$^1$ is a leaving group, with a compound of general formula IIIA,

A—OM$^1$                                            IIIA wherein

A is defined as for formula IB; and

M$^1$ represents a hydrogen or metal atom.

Advantageously, certain formula I compounds of this invention may be derivatized by conventional procedures known in the art to produce other compounds of formula I.

The aryl pyrimidine compounds of the present invention are effective for controlling insect and acarid pests. Those compounds are also effective for protecting growing or harvested crops from damage caused by insect and acarid attack and infestation.

Insects controlled by the aryl pyrimidine compounds of this invention include Lepidoptera such as tobacco budworms, cabbage loopers, cotton boll worms, beet armyworms, southern armyworms and diamondback moths; Homoptera such as aphids, leaf hoppers, plant hoppers and white flies; Thysanoptera such as thrips; Coleoptera such as boll weevils, Colorado potato beetles, southern corn rootworms, western corn rootworms and mustard beetles; and Orthoptera such as locusts, crickets, grasshoppers and cockroaches. Acarina controlled by the compounds of this invention include mites such as two-spotted spider mites, carmine spider mites, banks grass mites, strawberry mites, citrus rust mites and leprosis mites. Advantageously, it has been found that the compounds of the present invention are especially effective against tobacco budworms and southern armyworms.

In practice generally about 10 ppm to about 10,000 ppm and preferably about 100 ppm to about 5,000 ppm of a formula I aryl pyrimidine, dispersed in water or another liquid carrier, is effective when applied to plants or the soil in which the plants are growing to protect the plants from insect and acarid attack and infestation.

The aryl pyrimidine compounds of this invention are also effective for controlling insect and acarid pests when applied to the foliage of plants and/or to the soil or water in which said plants are growing in sufficient amount to provide a rate of about 0.1 kg/ha to 4.0 kg/ha of active ingredient.

While the compounds of this invention are effective for controlling insect and acarid pests when employed alone, they may also be used in combination with other biological chemicals, including other insecticides and acaricides. For example, the formula I compounds of this invention may be used effectively in conjunction or combination with pyrethroids, phosphates, carbamates, cyclodienes, endotoxin of bacillus thuringiensis (Bt), formamidines, phenol tin compounds, chlorinated hydrocarbons, benzoylphenyl ureas, pyrroles and the like.

The compounds of this invention may be formulated as emulsifiable concentrates, flowable concentrates or wettable powders which are diluted with water or other suitable polar solvent, generally in situ, and then applied as a dilute spray.

Said compounds may also be formulated in dry compacted granules, granular formulations, dusts, dust concentrates, suspension concentrates, microemulsions and the like all of which lend themselves to seed, soil, water and/or foliage applications to provide the requisite plant protection. Such formulations include the compounds of the invention admixed with agronomically acceptable inert, solid or liquid carriers.

In order to facilitate a further understanding of the invention, the following examples are presented primarily for the purpose of illustrating more specific details thereof. The invention should not be deemed limited by the examples as the full scope of the invention is defined in the claims.

EXAMPLE 1

1A Preparation of 4-(3,4-Dichlorophenyl)-2-Chloropyrimidine (METHOD A)

To a 1L 3-neck flask fitted with an addition funnel, N$_2$ inlet, magnetic stir bar and thermometer was added 15.26 (0.067 mol) of 3,4-dichloro-bromobenzene in 50–75 mL of anhydrous ether. The reaction was cooled to –90° C. and 96 mL of tert-butyllithium (1.7 M solution in pentane) slowly was added over a 0.5 hr while maintaining the temperature below –70° C. The reaction temperature was cooled to –80 to –90° C. and 2-chloropyrimidine (9.10 gm, 0.08 mol) dissolved in anhydrous THF was added. The reaction was stirred for about 2 h and 18 gms of DDQ, (0.077 mol) dissolved in anhydrous THF was added slowly, and the mixture was stirred for a 0.5 h. Three mL of H$_2$O containing 1 mL of HOAc in THF was added and the mixture stirred for 15 minutes. The reaction was diluted with 100 mL of H$_2$O and 100 mL of EtOAc and the mixture transferred to a separatory funnel. The organic layer was separated, dried, filtered and evaporated. The crude product was chromatographed and eluted with 30% EtOAc/heptane and triturated with Et$_2$O to yield 3.22 g of a white solid (20%) m.p. 126–127° C.

1B Preparation of 4-(3,4-Dichlorophenyl)-2-(3-Trifluoromethylphenoxy)-pyrimidine A 100 mL flask was charged with 1.2 g of 1A and the solid was dissolved in 8 mL of 8% trimethylamine/toluene solution and stirred overnight at room temperature. The resulting solid was collected by vacuum filtration to produce a quantitative yield of the trimethylammonium hydrochloride salt. (m.p. 179° C.) A 100 mL flask was charged 0.44 g (0.002 mol) of the salt, 0.26 g (1.25 eq) of K$_2$CO$_3$ and 5 mL of DMF and stirred for 15 min at RT. 0.25 g (1.1 eq) of m-trifluoromethyl-phenol was added and the reaction allowed to stir 36 h. The reaction was diluted with 5 mL of H$_2$O and 10 mL of EtOAc, transferred to separatory funnel and the organic layer was washed sequentially with 10 mL 10% NaOH and 10 mL of 10% HCl. The organic layer was dried (Na$_2$SO$_4$) filtered and evaporated to yield an oil. The crude product was chromatographed on silica gel and eluted with 20% EtOAc/heptane. The white solid was triturated in heptane to yield 0.26 g of white solid (45%, m.p. 106–106.5° C.)

EXAMPLE 2

Preparation of 2-(3-Trifluoromethyl-4-fluorophenoxy)-4-(4-fluorophenyl)pyrimidine (METHOD B)

2A Preparation of 4-Fluoroacetocyanoimine 10.4 g (75 mmol) of 4-fluoroacetophenone was converted to 2A by the procedure of Aumüller and Hünig, (*Angew, Chem. Int.Ed.* 23 (1974) 447–448). The crude reaction mixture was poured onto 1.5 L of crushed ice and the organic layer removed. The aqueous phase was re-extracted with 100 mL of $CH_2Cl_2$ and the combined organic phases washed with 50 mL water, dried ($MgSO_4$), filtered and evaporated to give 8.2 g (67%) of a white solid (m.p. 100–106° C.) which was sufficiently pure to use in the next step.

2B Preparation of 4-(4-Fluorophenyl)-2-chloro-pyrimidine

To a solution of 6.0 g of 2A in 150 mL of $CH_2Cl_2$ 15.5 g (155 mmoles) of phosphorous oxychloride and 5.95 g of DMF was added over 5 minutes. The resulting mixture is stirred at room temperature for 18 h, then quenched slowly with 50 mL of $H_2O$. The reaction mixture was transferred to a separatory funnel. The aqueous phase was extracted with 50 mL of $CH_2Cl_2$ and the combined organic phases washed sequentially with 50 mL $H_2O$ and 50 mL brine, dried, filtered and evaporated to a yellow solid. The crude product was purified by silica gel chromatography and eluted with 7/3 heptane/ethyl acetate to yield 1.24 g white solid. Re-crystallization of impure fractions yielded an additional 0.32 g of white crystalline solid. (m.p. 122–128° C.; 20%).

2C Preparation of 4-(4-Fluorophenyl)-2-(4-fluoro-3-trifluoromethylphenoxy)-pyrimidine To a solution of 0.60 g (2.87 mmol) of 2B in 15 ml of dimethylformamide was added 0.46 g of $K_2CO_3$ (3.3 mmol) and 0.60 g (3.3 mmol) of 4-fluoro-3-trifluoromethyl-phenol and the resulting mixture heated at 50° C. for 15 hr and 75° C. for 24 hrs. The cooled reaction mixture was poured into a separatory funnel containing 100 mL of ethyl acetate and washed with 2×50 mL water, 3×15 mL 2.5% NaOH solution, 1×30 mL brine, dried and evaporated in vacuuo to yield 1.95 g of a mobile yellow liquid. This material was filtered through a pad of silica and re-crystallized from heptane/ethyl acetate to give 0.49 g white crystalline solid (m.p. 69–74° C.; 48%)

EXAMPLE 3

Preparation of 2-(3-Trifluoromethyl-4-fluorophenoxy)-4-(3,4-dichlorophenyl)-5-chloropyrimidine (Method C)

3A Preparation of 2,4,5-Trichloropyrimidine 10 g (0.068 mol) of 5-chlorouracil in 20 mL $POCl_3$ (0.21 mol) was treated with 18 mL of N,N-diethylaniline (0.14 mol) at ambient temperature. The stirred mixture was heated to 100° C. for 4 h. Volatile solvents were removed in vacuo and the residue dissolved in 100 mL of diethyl ether and washed with 2×100 mL of ice cold 10% HCl solution, dried, filtered and evaporated to yield 8.54 g (82.9%) of 2,4,5-trichloropyrimidine as a colorless liquid. b.p. 73–75° C./3 Torr).

3B Preparation of 2,5-Dichloro-4-(3,4-dichlorophenyl) pyrimidine

A suspension of 0.19 g (0.5 mmol) of bis(benzo-nitril) dichloro-palladium (II) and 0.2 g 1,4-bis(di-phenylphosphino)butane in 10 mL of toluene was heated at reflux with stirring for 1 h under nitrogen. The suspension was cooled to room temperature. One gram (6.6 mmol) of 3A, 1.57 g of 3,4-dichlorobenzene boronic acid (8.2 mmol), 2.5 mL EtOH and 5 mL of 1 M $Na_2CO_3$ were added and the mixture heated to reflux for 20 h. The reaction mixture was cooled and diluted with 100 mL $Et_2O$. The suspension was filtered through a plug of silica gel and the cake washed with an additional 100 mL of $Et_2O$. The ether was evaporated and the residue chromatographed over silica gel (10% EtOAc/hexane). A fraction containing 0.72 g (32%) of 2,5-dichloro-4-(3,4-dichlorophenyl)pyrimidine was isolated as a white solid. (m.p. 125–126° C.)

3C Preparation of 2-(3-Trifluoromethyl-4-fluorophenoxy)-4-(3,4-dichlorophenyl)-5-chloropyrimidine To a solution of 0.5 g (1.7 mmol) of 3B in 10 mL of toluene was added 4.0 mL of 10% trimethylamine/toluene solution and the mixture stirred at room temperature for 20 min. To the resulting mixture was added 0.36 g (20 mmol) of 3-trifluoromethyl-4-fluorophenol and the mixture stirred overnight. The reaction mixture was diluted with $H_2O$ and transferred to a separatory funnel and extracted with 40 mL of methylene chloride. The organic layer was washed sequentially with 5% $NaHCO_3$ solution and water, dried and evaporated to yield 0.52 g (70.3%) of 2-(3-trifluoromethyl-4-fluorophenoxy)-4-(3,4-dichlorophenyl)-5-chloropyrimidine (m.p. 90–92)

EXAMPLE 4

Preparation of 2-(3-Trifluoromethyl-4-fluorophenoxy)-4-(3,4-dichlorophenyl)-6-trifluoromethylpyrimidine (METHOD D)

4A Preparation of 2-chloro-4-(3,4-dichlorophenyl)-6-trifluoromethylpyrimidine 4A was prepared from 2-chloro-4-trifluoromethyl-pyrimidine and 3,4-dichlorobromobenzene by the method reported for 1A. (Method A) $^1H$ NMR 1H, (8.29, 8.28, d) 1H, (8.01, 8.00, 7.98, 7.97, dd) 1H, (7.92, s) 1H, (7.66,7.63, d).

4B Preparation of 2-m-Trifluoromethylphenoxy-4-(3,4-dichlorophenyl)-6-trifluoromethylpyrimidine 4B was prepared from 4A as described for 1B. (Method A). This yielded 0.28 g of 4B m.p.111–112° C.

EXAMPLE 5

Preparation of 2-(3-Trifluoromethyl-4-fluorophenoxy)-4-(4-chlorophenyl)-6-cyanopyrimidine 5A Preparation of 2-Thiomethyl-4-(4-chlorophenyl)-6-chloro-pyrimidine 5A is prepared from 2-thiomethyl-4-chloropyrimidine and 4-chlorobromobenzene by the method reported for 1A: $^1H$ NMR: 2H(8.02, 8.00, d), 2H (7.48, 7.46, d), 1H(7.34, s)

5B Preparation of 2-Thiomethyl-4-(4-chlorophenyl)-6-cyano-pyrimidine

A solution of 1.5 g of 5A and 20 mL of an 8% solution of trimethylamine in toluene was stirred over night. The mixture was triturated with toluene, filtered to yield 2.08 g of the trimethylammonium salt: $^1H$ NMR 1H(9.27, s), 2H(8.61, 8.59, d), 2H (7.54, 7.52, d), 9H(4.11, s), 3H(2.69, s). To a solution of 1.0 g (3 mmol) of the ammonium salt in 10 mL of $CH_2Cl_2$ was added 0.47 g (3 mmol) of tetraethylammonium cyanide and the solution was stirred for 30 min. The solution was transferred to a separatory funnel and washed sequentially with 20 mL of $H_2O$ and 10 mL of brine, dried, filtered and evaporated to yield 0.46 g (48%) 5B: $^1H$ NMR 2H(8.06, 8.03, d), 1H(7.63, s), 2H(7.52, 7.50, d), 3H(2.64, s)

5C 2-(3-Trifluoromethyl-4-fluorophenoxy)-4-(4-chlorophenyl)-6-cyanopyrimidine

A solution of 0.54 g (2 mmol) of 5B, 0.72 g (2.0 eq) of MCPBA and 20 mL of $CH_2Cl_2$ was heated at reflux for 1 h, cooled to room temperature and transferred to a separatory funnel. The solution was washed with 10% $NaHCO_3$, dried ($Na_2SO_4$), filtered and evaporated to yield 0.27 g of the sulfoxide: $^1H$ NMR: 1H(8.18, s) 2H(8.185, 8.16, d), 2H (7.59, 7.57, d), 3H (3.46, s). A solution of 0.135 g (0.5 mmol) of the sulfoxide, 0.15 g (3 eq) of $Na_2CO_3$, 0.09 g (1.1 eq) of 3-trifluoro-methyl-4-fluorophenol and 5 mL of DMF were stirred for overnight at room temperature, heated to 60° C. for 4 h then cooled to room temperature. The resulting solution was diluted with 10 mL of EtOAc and washed sequentially with 10 mL of 10% NaOH and 10% HCl, dried, filtered and evaporated. The crude product was adsorbed on silica gel and 5C eluted with 20% EtOAc/hexane to yield 0.12 g of white solid, m.p. 131–132° C.

EXAMPLE 6

Preparation of 2-(3-Trifluoromethyl-4-fluorophenoxy)-4-(3,4-dichlorophenyl)-6-methylthio-pyrimidine and 2-(3-trifluoromethyl-4-fluorophenoxy)-4-(3,4-dichlorophenyl)-6-methylsulfonylpyrimidine 6A Preparation of 4-(3,4-Chlorophenyl)-2,6-dichloropyrimidine Prepared from 2, 4-dichloropyrimidine and 3,4-dichlorobromobenzene by the method reported for 1A: $^1$H NMR; 1H (8.21, 8.20, d) 1H (7.93, 7.92, 7.90, 7.89, dd), 1H (7.65, s), 1H (7.62, 7.59, dd)

6B 2-chloro-4-(3,4-Dichlorophenyl)-6-thiomethyl-4-pyrimidine

To a solution of 0.61 gm (2 mmol.) of 6A and 5 mL of dioxane was added 0.14 g (2 mmol) of NaSMe and the resulting solution was stirred at room temperature for 72 h. The reaction mixture was diluted with EtOAc and washed with 10 mL of H$_2$O, dried over Na$_2$SO$_4$, filtered and evaporated, then triturated with ether. The solid was collected by filtration to yield 0.30 g 6B: $^1$H NMR, 1H (8.156, 8.151, d), 1H(7.87, 7.86, 7.85, 7.84, dd), 1H(7.57, 7.55, d), 1H(7.42, s), 3H(2.63, s)

6C Preparation of 2-(3-Trifluoromethyl-4-fluorophenoxy)-4-(3,4-dichlorophenyl)-6-thiomethylpyrimidine 6B was converted to the trimethylammonium salt and subsequently reacted with 3-trifluoromethyl-4-fluorophenol by the procedure described for 1B to yield 0.19 g of 6C: m.p. 104–105° C., (54%).

6D Preparation of 2-(3-Trifluoromethyl-4-fluorophenoxy)-4-(3,4-dichlorophenyl)-6-methylsulfonyl-4-aryl Pyrimidine 6C was converted to 6D by oxidation with MCPBA as described for 5C. The reaction yielded 0.41 g (91%) of white solid 6D m.p. 137–138° C.

EXAMPLE 7

Preparation of 6-Amino-2-(3-trifluoromethyl-4-fluoro)aryloxy-4-aryl Pyrimidine

7A Preparation of 2-Thiomethyl-4-chloro-6-tert-butoxycarbonylaminopyrimidine

A solution of 5.06 g (0.03 mol.) of 4-amino-6-chloro-2-(methylthio)pyrimidine, 9 mL (2 eq) of Et$_3$N, 6.9 g (0.03 mol) of di-tert-butyl-dicarbonate and 20 mL of THF was refluxed for 2 days. The reaction was cooled to room temperature, evaporated and the residue adsorbed on silica gel and eluted with 10% EtOAc/heptane to yield 5.86 g (74%) of the protected amine: $^1$H NMR, 1H (7.64, s), 1H(7.28, broad s), 3H(2.50), 9H(1.52, s)

7B Preparation of 6-NH-Boc-2-thiomethyl-4-(3,4-dichlorophenyl)pyrimidine

A round bottom flask was charged with 0.21 g (0.5 mmol.) of bis(benzonitrile)dichloro palladium, 0.23 g (0.5 mmol.) of bis(diphenyl phosphorus)butane in 10 mL of toluene and refluxed for 2 h. The solution was cooled to room temperature and and 1.3 g of 3,4-dichlorophenyl boronic acid, 1.5 g of 7A, 5 mL 1M Na$_2$CO$_3$ and 20 mL of EtOH were added and the solution was refluxed for an additional 2 h. The reaction mixture was cooled to room temperature. On standing overnight the a solid precipitated which was filtered and discarded. The mother liquor was concentrated and on standing formed a solid that was triturated with heptane. The solid was filtered to yield 1.19 gm (57%) of white solid: m.p.158–159° C.

7C Preparation of 6-NH-Boc-2-methylsulfonyl-4-(3,4-dichlorophenyl)pyrimidine

Prepared by the as described for 6D: m.p. 185–1860° C.

7D Preparation of 6-Amino-2-(3-trifluoromethyl-phenoxy)-4-(3,4-dichlorophenyl)pyrimidine A round-bottom flask was charged with 0.73 g of 7C, 15 mL of DMF and 0.55 g (3 eq.) of Na$_2$CO$_3$ and stirred for 15 m. To the solution was added 0.31 g (1.1 eq) of 3-trifluoromethylphenol and the mixture heated to reflux for 4 h, cooled and allowed to stand overnight. The solution was diluted with 10 mL of water and transferred to a separatory funnel and washed with 30 mL of EtOAc. The organic layer was sequentially washed with 10 mL Of 10% NaOH, 10% HCl, dried, filtered and evaporated. The crude product was absorbed on silica gel and eluted with 50% EtOAc/heptane 7E Preparation of 6-Methyl-2-(3-trifluoromethyl-4-fluorophenoxy)-4-(3,4-dichlorophenyl)

Prepared by the procedure described for 7D utilizing 4-methyl-6-chloro-2-(methylthio)pyrimidine as the starting material

EXAMPLE 8

Preparation of 2-[N-Methyl-N-(4-fluoro-3-trifluoromethylphenyl)amino]-4-(4-fluoro-3-trifluoromethylphenyl)-pyrimidine (METHOD E)

A round-bottom flask was charged with 1.03 g of 2-chloro-4-(4-fluoro-3-trifluoromethylphenyl)-pyrimidine and 0.82 g of 4-fluoro-3-trifluoromethyl-N-methylaniline and heated to 126° C. for 1.5 h. The reaction mixture melted and subsequently thickened. After standing overnight, the mixture was partitioned between 20 mL of EtOAc and 20 mL of NaHCO$_3$. The organic phase was separated, dried, filtered and evaporated. The crude product was adsorbed onto silica gel and eluted with 50% EtOAc/heptane to yield 0.67 g of an oil which solidified on standing: m.p. 83–84° C.

EXAMPLE 9

Preparation of 4-Methyl-5-phenyl-3-(3-trifluoro-methylphenoxy)-pyrimidine

9A Preparation of 2-Amino-1-methyl-2-phenyl-acrylonitrile

A round-bottom flask was charged with 7.2 g of 1-benzoylpropionitrile, 200 ml of ethanol and 10.0 g of ammonium acetate and heated to reflux for 1.5 h. Ethanol was distilled off. The residue was diluted with 200 ml of EtOAc and washed with 100 mL of H$_2$O twice, dried over MgSO$_4$, filtered and evaporated. The product was obtained as an amber oil (7.15 g) which solidified on standing (m.p. 68–86° C.).

9B Preparation of 2-Chloro-4-methyl-5-phenyl-pyrimidine

A round-bottom flask was charged with 1.5 g of crude 9A, 1.8 ml of phosphorous oxychloride, 1.5 ml of dimethylformamide and 30 ml of acetonitrile and stirred for 30 minutes at 30° C. and subsequently heated to reflux for 6.5 h. The reaction was diluted with 150 ml of EtOAc and washed with 50 mL of H$_2$O twice, dried over MgSO$_4$, filtered and evaporated. The crude product was adsorbed onto silica gel and eluted with 50% EtOAc/heptane to yield 0.61 g of a yellow liquid.

9C Preparation of 4-(4-Fluorophenyl)-2-(4-fluoro-3-trifluorophenoxy)-pyrimidine To a solution of 0.61 g of 9B in 30 ml of dimethylformamide was added 0.5 g of $K_2CO_3$ and 0.58 g of 3-trifluoromethylphenol and the resulting mixture was heated at 60° C. for 15 hr and 75° C. for 24 h. The cooled reaction mixture was poured into a separatory funnel containing 100 mL of ethyl acetate and washed with 2×50 mL water, 3×15 mL 2.5% NaOH solution, 1×30 mL brine, dried and evaporated in vacuuo to yield 0.93 g of a yellow oil.

Using essentially the same procedure, the compounds given in tables I to III are obtained:

TABLE I

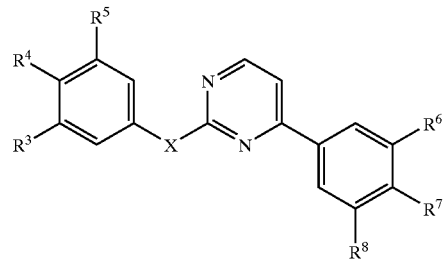

| Compound No. | $R^3$ | $R^4$ | $R^5$ | $R^6$ | $R^7$ | $R^8$ | X | Method |
|---|---|---|---|---|---|---|---|---|
| 1 | $CF_3$ | Cl | H | H | Cl | H | O | A |
| 2 | $CF_3$ | H | H | H | Cl | H | O | A |
| 3 | $CF_3$ | $NO_2$ | H | H | Cl | H | O | A |
| 4 | $CF_3$ | F | H | H | Cl | H | O | A |
| 5 | $CF_3$ | H | H | H | H | H | O | A |
| 6 | $CF_3$ | F | H | H | H | H | O | A |
| 7 | Cl | $CF_3$ | H | H | H | H | O | A |
| 8 | $CF_3$ | $NO_2$ | H | H | H | H | O | A |
| 9 | $CF_3$ | H | H | H | $NO_2$ | H | O | B |
| 10 | $CF_3$ | F | H | H | $NO_2$ | H | O | B |
| 11 | $CF_3$ | $NO_2$ | H | H | Et | H | O | A |
| 12 | Cl | Cl | H | H | Et | H | O | A |
| 13 | Cl | F | H | H | Et | H | O | A |
| 14 | $CF_3$ | F | H | H | Et | H | O | A |
| 15 | $CF_3$ | H | H | H | Et | H | O | A |
| 16 | $CF_3$ | F | H | H | Et | H | NH | A |
| 17 | $CF_3$ | Cl | H | H | Et | H | O | A |
| 18 | Cl | Cl | H | H | H | $CF_3$ | O | A |
| 19 | $CF_3$ | $NO_2$ | H | H | H | $CF_3$ | O | A |
| 20 | Cl | Cl | H | H | H | $CF_3$ | O | A |
| 21 | $CF_3$ | F | H | H | H | $CF_3$ | O | A |
| 22 | $CF_3$ | F | H | H | F | H | O | B |
| 23 | $CF_3$ | H | H | H | F | H | O | B |
| 24 | $CF_3$ | F | H | H | t-Bu | H | O | A |
| 25 | $CF_3$ | Cl | H | H | t-Bu | H | O | A |
| 26 | $CF_3$ | $NO_2$ | H | H | t-Bu | H | O | A |
| 27 | Cl | Cl | H | H | t-Bu | H | O | A |
| 28 | Cl | Cl | H | H | $CF_3$ | H | O | A |
| 29 | $CF_3$ | F | H | H | $CF_3$ | H | O | A |
| 30 | $CF_3$ | H | H | H | $CF_3$ | H | O | A |
| 31 | Cl | F | H | H | $CF_3$ | H | O | A |
| 32 | $CF_3$ | Cl | H | H | $CF_3$ | H | O | A |
| 33 | $CF_3$ | $NO_2$ | H | H | $CF_3$ | H | O | A |
| 34 | $CF_3$ | F | H | H | MeO | H | O | A |
| 35 | $CF_3$ | Cl | H | H | MeO | H | O | A |
| 36 | $CF_3$ | H | H | H | MeO | H | O | A |
| 37 | $CF_3$ | F | H | H | H | $OCF_3$ | O | A |
| 38 | $CF_3$ | H | H | H | H | $OCF_3$ | O | A |
| 39 | $CF_3$ | Cl | H | H | H | $OCF_3$ | O | A |
| 40 | $CF_3$ | $NO_2$ | H | H | H | $OCF_3$ | O | A |
| 41 | Cl | H | Cl | H | H | $OCF_3$ | O | A |
| 42 | $CF_3$ | H | $CF_3$ | H | H | $OCF_3$ | O | A |
| 43 | Cl | Cl | H | H | H | $OCF_3$ | O | A |
| 44 | Cl | H | Cl | H | $OCF_3$ | H | O | A |
| 45 | $CF_3$ | H | $CF_3$ | H | $OCF_3$ | H | O | A |
| 46 | $CF_3$ | Cl | H | H | $OCF_3$ | H | O | A |
| 47 | $CF_3$ | F | H | H | $OCF_3$ | H | O | A |

TABLE I-continued

| Compound No. | $R^3$ | $R^4$ | $R^5$ | $R^6$ | $R^7$ | $R^8$ | X | Method |
|---|---|---|---|---|---|---|---|---|
| 48 | $CF_3$ | H | H | H | $OCF_3$ | H | O | A |
| 49 | $CF_3$ | $NO_2$ | H | H | $OCF_3$ | H | O | A |
| 50 | Cl | Cl | H | H | $OCF_3$ | H | O | A |
| 51 | $CF_3$ | Cl | H | $CF_3$ | H | F | O | A |
| 52 | $CF_3$ | H | H | $CF_3$ | H | F | O | A |
| 53 | $CF_3$ | F | H | $CF_3$ | H | F | O | A |
| 54 | H | H | H | $CF_3$ | H | F | O | A |
| 55 | Cl | F | H | H | $OCF_3$ | H | O | A |
| 56 | Cl | F | H | $CF_3$ | H | F | O | A |
| 57 | $CF_3$ | $NO_2$ | H | $CF_3$ | H | F | O | A |
| 58 | Cl | Cl | H | $CF_3$ | H | F | O | A |
| 59 | Cl | H | Cl | $CF_3$ | H | F | O | A |
| 60 | $CF_3$ | H | $CF_3$ | $CF_3$ | H | F | O | A |
| 61 | $CF_3$ | H | H | F | H | F | O | A |
| 62 | $CF_3$ | F | H | F | H | F | O | A |
| 63 | H | H | H | $CF_3$ | Cl | Cl | O | A |
| 64 | F | H | H | $CF_3$ | Cl | Cl | O | A |
| 65 | Cl | H | H | F | Cl | Cl | O | A |
| 66 | $CF_3$ | F | H | H | H | Cl | O | A |
| 67 | $CF_3$ | H | H | H | H | Cl | O | A |
| 68 | $CF_3$ | F | H | H | H | F | O | A |
| 69 | $CF_3$ | H | H | H | H | F | O | A |
| 70 | $CF_3$ | F | H | H | F | $CF_3$ | O | A |
| 71 | $CF_3$ | H | H | H | F | $CF_3$ | O | A |
| 72 | Cl | Cl | H | H | H | F | O | A |
| 73 | Cl | Cl | H | H | F | $CF_3$ | O | A |
| 74 | $CF_3$ | F | H | H | F | $CF_3$ | NMe | E |
| 75 | $CF_3$ | H | H | H | F | $CF_3$ | NMe | E |
| 76 | $CF_3$ | H | H | H | F | $CF_3$ | NMe | E |
| 77 | $CF_3$ | H | H | H | Cl | F | O | A |
| 78 | $CF_3$ | F | H | H | Cl | F | O | A |
| 79 | $CF_3$ | Cl | H | H | Cl | F | O | A |
| 80 | $CF_3$ | H | H | Cl | H | Cl | O | A |

TABLE II

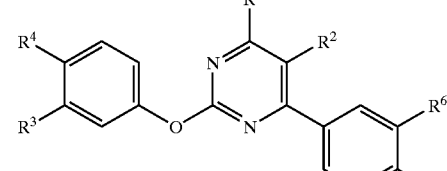

| Compound No. | $R_1$ | $R_2$ | $R_3$ | $R_4$ | $R_6$ | $R_7$ |
|---|---|---|---|---|---|---|
| 81 | H | Cl | $CF_3$ | F | H | $CF_3$ |
| 82 | H | Et | $CF_3$ | F | F | Cl |
| 83 | H | Et | $CF_3$ | F | H | Cl |
| 84 | $CF_3$ | H | $CF_3$ | F | Cl | Cl |
| 85 | SMe | H | $CF_3$ | F | Cl | Cl |
| 86 | H | $NO_2$ | $CF_3$ | F | Cl | F |
| 87 | H | Me | $CF_3$ | F | H | F |
| 88 | H | F | F | $CF_3$ | Cl | F |
| 89 | H | Cl | $CF_3$ | F | Cl | F |
| 90 | H | CN | $CF_3$ | F | Cl | F |
| 91 | CN | H | $CF_3$ | F | H | Cl |

TABLE II-continued

| Compound No. | $R_1$ | $R_2$ | $R_3$ | $R_4$ | $R_6$ | $R_7$ |
|---|---|---|---|---|---|---|
| 92 | $SO_2Me$ | H | $CF_3$ | F | Cl | Cl |
| 93 | H | Cl | $CF_3$ | F | Cl | Cl |
| 94 | H | F | $CF_3$ | F | F | Cl |
| 95 | H | Me | $CF_3$ | F | Cl | Cl |
| 96 | H | F | $CF_3$ | F | Cl | F |
| 97 | Me | H | $CF_3$ | F | Cl | Cl |
| 98 | H | Cl | $CF_3$ | F | Cl | Me |
| 99 | CN | H | $CF_3$ | F | Cl | H |
| 100 | $NH_2$ | H | $CF_3$ | H | Cl | Cl |
| 101 | NHboc | H | $CF_3$ | H | Cl | Cl |
| 102 | Me | H | $CF_3$ | F | Cl | H |
| 103 | Me | H | $CF_3$ | F | H | Cl |
| 104 | SMe | H | $CF_3$ | F | Cl | H |
| 105 | SMe | H | $CF_3$ | F | H | Cl |
| 106 | $CF_3$ | H | $CF_3$ | F | Cl | H |
| 107 | Me | H | $CF_3$ | F | Cl | Cl |

TABLE III

| Compound No. | $R^1$ | $R^2$ | $R^3$ | $R^4$ | $R^6$ | $R^7$ |
|---|---|---|---|---|---|---|
| 108 | SMe | H | $CF_3$ | H | $CF_3$ | H |
| 109 | H | H | $CF_3$ | H | $CF_3$ | H |
| 110 | Cl | H | $CF_3$ | H | $CF_3$ | H |
| 111 | $NMe_2$ | H | $CF_3$ | H | $CF_3$ | H |
| 112 | H | H | $CF_3$ | F | $CF_3$ | H |
| 113 | SMe | H | $CF_3$ | Cl | $CF_3$ | H |
| 114 | SMe | H | $CF_3$ | F | H | Cl |
| 115 | H | H | $CF_3$ | F | H | Cl |
| 116 | H | H | $CF_3$ | H | H | Cl |
| 117 | H | H | $CF_3$ | H | $CF_3$ | H |
| 118 | SMe | H | $CF_3$ | H | H | Cl |
| 119 | SMe | H | Cl | H | H | Cl |
| 120 | H | H | Cl | H | H | Cl |
| 121 | SMe | H | $CF_3$ | Cl | H | Cl |
| 122 | H | H | $CF_3$ | Cl | H | Cl |
| 123 | CN | H | $CF_3$ | Cl | H | Cl |
| 124 | SMe | H | $CF_3$ | H | Cl | H |
| 125 | Sme | H | $CF_3$ | Cl | Cl | H |
| 126 | H | H | $CF_3$ | Cl | Cl | H |
| 127 | H | H | $CF_3$ | H | Cl | H |
| 128 | H | H | $CF_3$ | H | H | H |
| 129 | H | H | $CF_3$ | F | H | $CF_3$ |
| 130 | H | H | $CF_3$ | F | H | H |
| 131 | H | Et | $CF_3$ | H | H | Cl |
| 132 | H | Et | $CF_3$ | F | H | Cl |
| 133 | H | H | $CF_3$ | $NO_2$ | H | H |
| 134 | H | CHO | $CF_3$ | H | H | H |
| 135 | H | H | F | $CF_3$ | H | F |
| 136 | H | H | $CF_3$ | H | H | F |
| 137 | H | H | F | H | H | Cl |
| 138 | H | H | H | $CF_2$ | H | Cl |
| 139 | H | H | F | F | H | Cl |
| 140 | H | H | $NO_2$ | H | H | Cl |
| 141 | H | H | CN | H | H | Cl |
| 142 | H | H | F | H | H | Cl |
| 143 | H | H | OMe | H | H | Cl |
| 144 | H | H | $CF_3$ | H | H | $CF_3$ |
| 145 | H | H | $CF_3$ | Cl | H | $CF_3$ |
| 146 | H | H | $CF_3$ | $NO_2$ | H | Cl |
| 147 | H | H | $CF_3$ | H | H | Me |
| 148 | H | H | $CF_3$ | Cl | H | Me |
| 149 | H | H | $CF_3$ | F | H | Me |
| 150 | H | H | Cl | F | H | Cl |
| 151 | H | H | Cl | Cl | H | Cl |
| 152 | H | H | $CF_3$ | H | H | OMe |
| 153 | H | H | $CF_3$ | F | H | OMe |
| 154 | H | H | $CF_3$ | H | Cl | Cl |
| 155 | H | H | $CF_3$ | F | Cl | Cl |
| 156 | H | Et | $CF_3$ | F | $CF_3$ | H |
| 157 | H | Et | $CF_3$ | H | $CF_3$ | H |
| 158 | H | Et | $CF_3$ | Cl | $CF_3$ | H |
| 159 | H | n-Pr | $CF_3$ | H | $CF_3$ | H |
| 160 | H | n-Pr | $CF_3$ | F | $CF_3$ | H |
| 161 | H | H | $CF_3$ | H | H | Br |
| 162 | H | H | $CF_3$ | F | H | Br |
| 163 | H | Me | $CF_3$ | H | H | H |

EXAMPLE 10

Insecticidal and Acaricidal Evaluation of Test Compounds

Test solutions are prepared by dissolving the test compound in a 35% acetone in water mixture to give a concentration of 10,000 ppm. Subsequent dilutions are made with water as needed.

*Spodoptera Eridania*, 3rd Instar Larvae, Southern Armyworm (SAW)

A Sieva lima bean leaf expanded to 7–8 cm in length is dipped in the test solution with agitation for 3 seconds and allowed to dry in a hood. The leaf is then placed in a 100×10 mm petri dish containing a damp filter paper on the bottom and ten 3rd instar caterpillars. At 5 days, observations are made of mortality, reduced feeding, or any interference with normal molting.

*Diabrotica Virgifera Virgifera* Leconte, 3rd Instar Western Corn Rootworm (WCR)

One cc of fine talc is placed in a 30 mL wide-mouth screw-top glass jar. One mL of the appropriate acetone test solution is pipetted onto the talc so as to provide 1.25 mg of active ingredient per jar. The jars are set under a gentle air flow until the acetone is evaporated. The dried talc is loosened, 1 cc of millet seed is added to serve as food for the insects and 25 mL of moist soil is added to each jar. The jar is capped and the contents thoroughly mixed mechanically. Following this, ten 3rd instar rootworms are added to each jar and the jars are loosely capped to allow air exchange for the larvae. The treatments are held for 5 days when mortality counts are made. Missing larvae are presumed dead, since they decompose rapidly and can not be found. The concentrations of active ingredient used in this test correspond approximately to 50 kg/ha.

*Aphis Fabae*, Mixed Instar, *Bean Aphid* (BA)

Pots containing single nasturtium plants (Tropaeolum sp.) about 5 cm tall are infested with about 100–200 aphids one day before the test. Each pot is sprayed with the test solution for 2 revolutions of a 4 rpm turntable in a hood. The spray is directed to give complete coverage of the plants and aphids. The sprayed pots are set on their sides on white trays and held for 2 days, following which mortality estimates are made. Essentially the same method is used with respect to cotton aphid (CA).

*Tetranychus Urticae* (OP-resistant strain), 2-spotted Spider Mite (TSM)

Sieva lima bean plants with primary leaves expanded to 7–8 cm are selected and cut back to one plant per pot. A small piece is cut from an infested leaf taken from the main colony and placed on each leaf of the test plants. This is done about 2 hours before treatment to allow the mites to move over to the test plant to lay eggs. The size of the cut, infested leaf is varied to obtain about 100 mites per leaf. At the time of test treatment, the piece of leaf used to transfer the mites is removed and discarded. The newly-infested plants are dipped in the test solution for 3 seconds with agitation and set in the hood to dry. After 2 days, one leaf is removed and mortality counts are made.

The tests are rated according to the scale shown below and the data obtained are shown in Table IV.

Rating Scale

A 0–45% kill
B 45–75% kill
C 76–100% kill

TABLE IVa

Insecticidal Activity Of Test Compounds Against Bean Aphid (300 ppm)

| Compound Number | BA AD-FOLIAR 300 (ppm) |
|---|---|
| 5 | A |
| 9 | B |
| 13 | C |
| 15 | C |
| 17 | C |
| 18 | A |
| 19 | A |
| 20 | B |
| 21 | A |
| 22 | B |
| 24 | A |
| 25 | A |
| 26 | B |
| 27 | B |
| 28 | A |
| 29 | A |

TABLE IVa-continued

Insecticidal Activity Of Test Compounds Against Bean Aphid (300 ppm)

| Compound Number | BA AD-FOLIAR 300 (ppm) |
|---|---|
| 30 | A |
| 31 | B |
| 32 | B |
| 33 | B |
| 37 | A |
| 38 | A |
| 42 | B |
| 43 | C |
| 45 | C |
| 46 | B |
| 47 | A |
| 48 | B |
| 49 | B |
| 50 | B |
| 53 | C |
| 54 | C |
| 55 | A |
| 58 | C |
| 59 | B |
| 61 | C |
| 62 | B |
| 63 | A |
| 71 | C |
| 108 | B |
| 109 | B |
| 111 | C |
| 128 | B |
| 129 | B |
| 130 | A |
| 132 | C |
| 135 | A |
| 137 | C |
| 139 | C |
| 140 | A |
| 141 | B |
| 142 | C |
| 143 | C |
| 144 | B |
| 145 | B |
| 147 | C |
| 150 | B |
| 151 | B |
| 153 | B |
| 154 | B |
| 155 | C |
| 156 | C |
| 157 | B |
| 161 | C |
| 163 | A |

TABLE IVb

Insecticidal Activity of Test Compounds against Southern Army Worm (1000 ppm)

| Compound Number | SAW $2^{ND}$-FOLIAR 1000 (ppm) |
|---|---|
| 1 | A |
| 2 | A |
| 3 | B |
| 4 | A |
| 5 | A |
| 6 | A |
| 8 | A |
| 82 | C |

TABLE IVb-continued

Insecticidal Activity of Test Compounds against Southern Army Worm (1000 ppm)

| Compound Number | SAW 2<sup>ND</sup>-FOLIAR 1000 (ppm) |
|---|---|
| 12 | C |
| 13 | C |
| 18 | A |
| 20 | A |
| 21 | A |
| 22 | A |
| 23 | A |
| 29 | A |
| 30 | A |
| 32 | A |
| 37 | C |
| 40 | A |
| 44 | A |
| 46 | B |
| 47 | A |
| 48 | A |
| 50 | A |
| 51 | B |
| 52 | A |
| 53 | A |
| 54 | C |
| 55 | A |
| 60 | C |
| 62 | C |
| 109 | A |
| 110 | C |
| 112 | A |
| 115 | A |
| 116 | A |
| 117 | A |
| 119 | B |
| 122 | B |
| 129 | A |
| 131 | A |
| 132 | A |
| 135 | A |
| 136 | A |
| 144 | A |
| 145 | A |
| 155 | A |
| 156 | A |
| 157 | A |
| 158 | A |
| 159 | A |
| 160 | A |
| 161 | A |
| 162 | A |

TABLE IVc

Insecticidal Activity of Test Compounds against Two-spotted Spider Mite (300 ppm)

| Compound Number | TSM AD-FOLIAR 300 (ppm) |
|---|---|
| 2 | C |
| 4 | A |
| 5 | B |
| 12 | C |
| 15 | C |
| 18 | A |
| 21 | A |
| 22 | A |
| 23 | A |
| 29 | B |

TABLE IVc-continued

Insecticidal Activity of Test Compounds against Two-spotted Spider Mite (300 ppm)

| Compound Number | TSM AD-FOLIAR 300 (ppm) |
|---|---|
| 30 | B |
| 37 | A |
| 38 | A |
| 39 | A |
| 41 | A |
| 42 | C |
| 43 | C |
| 47 | B |
| 48 | B |
| 49 | B |
| 54 | C |
| 55 | A |
| 63 | A |
| 64 | A |
| 66 | A |
| 67 | A |
| 68 | B |
| 70 | B |
| 71 | A |
| 78 | B |
| 115 | B |
| 116 | B |
| 128 | C |
| 132 | B |
| 135 | A |
| 136 | A |
| 140 | B |
| 142 | C |
| 147 | C |
| 150 | C |
| 156 | B |
| 157 | B |
| 159 | B |
| 160 | A |
| 163 | B |

TABLE IVd

Insecticidal Activity of Test Compounds against Western Corn Rootworm (50 ppm)

| Compound Number | WCR 2<sup>ND</sup>-SOIL 50 (ppm) |
|---|---|
| 5 | C |
| 7 | C |
| 12 | C |
| 19 | C |
| 21 | C |
| 22 | C |
| 23 | B |
| 24 | C |
| 27 | C |
| 35 | C |
| 37 | B |
| 38 | C |
| 39 | B |
| 42 | B |
| 43 | C |
| 50 | C |
| 51 | C |
| 55 | C |
| 56 | B |
| 57 | C |
| 57 | C |
| 59 | C |

TABLE IVd-continued

Insecticidal Activity of Test Compounds against Western Corn Rootworm (50 ppm)

| Compound Number | WCR 2ND-SOIL 50 (ppm) |
| --- | --- |
| 60 | C |
| 64 | C |
| 66 | C |
| 85 | C |
| 92 | C |
| 114 | C |
| 125 | B |
| 129 | B |
| 131 | C |
| 139 | C |
| 144 | C |
| 145 | C |
| 157 | C |
| 158 | C |
| 160 | C |
| 163 | C |

TABLE IVe

Insecticidal Activity of Test Compounds against Cotton Aphid (300 ppm)

| Compound Number | CA-FOLIAR 300 (ppm) |
| --- | --- |
| 63 | C |
| 64 | A |
| 66 | A |
| 67 | C |
| 68 | C |
| 71 | B |
| 78 | B |

What is claimed is:

1. A method for the control of insect or acarid pests which comprises contacting said pests or their food supply, habitat or breeding grounds with a pesticidally effective amount of a compound having the structural formula I

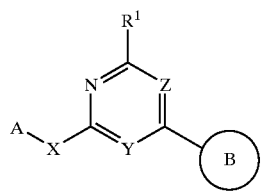

(I)

wherein

A and B each independently represent an optionally substituted aryl group, with a proviso that A is not 4-nitrophenyl;

$R^1$ represents a hydrogen or halogen atom or an optionally substituted alkyl, alkenyl, alkinyl, alkoxy, alkoxyalkyl, alkoxyalkoxy group; or an alkylthio group, alkylsulphinyl or alkylsulphonyl group, an amino, alkylamino or dialkylamino group or a cyano, nitro, haloalkyl, haloalkoxy, haloalkylthio or $SF_5$ group, one of Y and Z represents N and the other represents $CR^2$, in which $R^2$ has the meaning given for $R^1$;

X represents O or NR, in which R represents a hydrogen atom or an alkyl group.

2. A method as claimed in claim 1, wherein A represents a phenyl group being substituted by one or more of the same or different substituents selected from halogen atoms, alkyl, alkoxy, cyano, nitro, haloalkyl, haloalkoxy, alkylthio, haloalkylthio, alkylsulphinyl, alkylsulphonyl and $SF_5$ groups.

3. A method as claimed in claim 2, wherein A has a substituent in the meta-position relative to the point of attachment.

4. A method as claimed in claim 3, wherein A is meta-substituted by a fluorine or chlorine atom, or a trifluoromethyl, trifluoromethoxy or difluoromethoxy group.

5. A method for the control of insect or acarid pests which comprises contacting said pests or their food supply, habitat or breeding grounds with a pesticidally effective amount of a compound having structural formula I

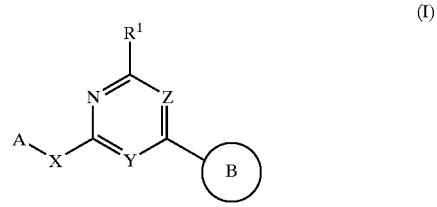

(I)

wherein A represents an optionally substituted aryl group and B represents a phenyl group being substituted by one or more of the same or different substituents selected from halogen atoms, alkyl, alkoxy, cyano, nitro, haloalkyl, haloalkoxy, alkylthio, haloalkylthio, alkylsulphinyl, alkylsulphonyl and $SF_5$ groups;

$R^1$ represents a hydrogen or halogen atom or an optionally substituted alkyl, alkenyl, alkinyl, alkoxy, alkoxyalkyl, alkoxyalkoxy group; or an alkylthio group, alkylsulphinyl or alkylsulphonyl group, an amino, alkylamino or dialkylamino group or a cyano, nitro, haloalkyl haloalkoxy, haloalkylthio or $SF_5$ group, one of Y and Z represents N and the other represents $CR^2$, in which $R^2$ has the meaning given for $R^1$;

X represents O or NR, in which R represents a hydrogen atom or an alkyl group.

6. A method as claimed in claim 5, wherein B is meta- or para-substitute by a fluorine or chlorine atom, or a trifluoromethyl, trifluoromethoxy or difluoromethoxy group.

7. A method for the protection of growing plants from attach or infestation by insect or acarid pests which comprises applying to the foliage of the plants, or to the soil or water in which they are growing, a pesticidally effective amount of a compound having the structural formula I given in claim 1.

8. The method according to claim 7 wherein the compound is applied to the plants, or to the soil or water in which they are growing, at a rate of about 0.1 kg/ha to 4.0 kg/ha.

* * * * *

UNITED STATES PATENT AND TRADEMARK OFFICE
CERTIFICATE OF CORRECTION

PATENT NO. : 6,440,984 B1 Page 1 of 1
DATED : August 27, 2002
INVENTOR(S) : Wood et al.

It is certified that error appears in the above-identified patent and that said Letters Patent is hereby corrected as shown below:

Column 20,
Line 54, "attach" should be -- attack --.

Signed and Sealed this

Thirty-first Day of December, 2002

JAMES E. ROGAN
*Director of the United States Patent and Trademark Office*